United States Patent [19]
Katschnig et al.

[11] Patent Number: 5,403,564
[45] Date of Patent: Apr. 4, 1995

[54] APPARATUS FOR HEATING AND THERMAL DECONTAMINATING A PUMPABLE OR POURABLE MATERIAL

[75] Inventors: Helmut Katschnig, Burgstrasse 108, 8750 Judenburg; Wolfgang Stegmüller, St. Peter/Judenburg; Ernst Gruber, Judenburg, all of Austria

[73] Assignee: Helmut Katschnig, Austria

[21] Appl. No.: 166,544

[22] Filed: Dec. 14, 1993

[30] Foreign Application Priority Data

May 5, 1993 [AT] Austria .................................. 884/93

[51] Int. Cl.⁶ .......................... A61L 9/00; A21D 6/00; B23K 15/10; D06F 75/26
[52] U.S. Cl. ............................................ 422/307; 422/5; 422/21; 422/28; 422/905; 426/237; 426/241; 219/248; 219/686; 392/320; 392/471
[58] Field of Search ................. 422/307, 905, 21, 5, 422/28, 38; 219/248, 251, 10.55 A, 10.55 R, 678, 687, 688, 702, 704, 710, 711; 392/314, 320, 471, 481; 426/237, 241

[56] References Cited

U.S. PATENT DOCUMENTS

| | | | |
|---|---|---|---|
| 3,535,482 | 10/1970 | Kluck | 219/687 |
| 3,816,689 | 6/1974 | Long | 219/687 |
| 4,152,567 | 5/1979 | Mayfield | 219/688 |
| 4,288,674 | 9/1981 | Councell | 219/687 |
| 4,313,786 | 2/1982 | Smith | 159/22 |
| 4,358,652 | 11/1982 | Kaarup | 219/687 |
| 4,417,116 | 11/1983 | Black | 219/687 |
| 4,480,993 | 11/1984 | Guiriel | 422/307 |
| 4,839,142 | 6/1989 | Charm | 422/21 |
| 5,180,896 | 1/1993 | Gibby et al. | 219/687 |
| 5,210,386 | 11/1993 | Sprunger | 219/688 |
| 5,246,674 | 9/1993 | Katschnig et al. | 422/302 |

Primary Examiner—Robert J. Warden
Assistant Examiner—Christopher Y. Kim
Attorney, Agent, or Firm—Henry M. Feiereisen

[57] ABSTRACT

Apparatus for heating and thermal decontaminating, e.g. sterilizing, pasteurizing and/or disinfecting, pumpable or pourable material, includes a microwave unit forming a treatment chamber for receiving the material transported along a passageway and for subjecting the material to microwave radiation. Two pumps are respectively situated upstream and downstream of the treatment chamber, with a pressure sensor being arranged between the pumps for generating a a signal commensurate with the pressure in the passageway between the pumps. The signal is transmitted from the pressure sensor to a control unit which is operatively connected to both pumps.

13 Claims, 2 Drawing Sheets

APPARATUS FOR HEATING AND THERMAL DECONTAMINATING A PUMPABLE OR POURABLE MATERIAL

BACKGROUND OF THE INVENTION

The present invention refers to an apparatus for heating and thermal decontaminating, such as sterilizing, pasteurizing and/or disinfecting, a pumpable and pourable material, of the type including a microwave device with a treatment chamber for receiving the material being treated.

European patent No. EP-A 0116 921 describes a microwave sterilizer for sterilizing a connector or coupling that interconnects a first conduit from a source of liquid to be infused into a living body to a second conduit implanted in the body. These couplings are medical connections between extracorporeal and intracorporeal devices i.e. a system for peritoneal dialysis. This reference is silent as to a pressure sterilization; Rather, this prior art is concerned only with sterilization of a first charge of liquid in order to prevent infection within the body.

German patent No. DE-A1 34 30 673 discloses an apparatus for pasteurizing and sterilizing pourable or bulky material which is advanced through a treatment chamber by upper and lower conveyor belts, with the material being subjected to microwave radiation in the treatment chamber to kill present bacteria, fungi or the like. Also this apparatus operates at normal pressure.

U.S. Pat. No. 4,417,116 describes a microwave water-heating apparatus in form of a flow heater, with a microwave chamber housing a polyhedron fluid conductor body which has a plurality of parallel bores formed parallel to the axis of the conductor body for fluid to pass through. These bores end at each axial end in a common chamber, with water entering one chamber and being discharged through the other chamber. This apparatus operates at normal pressure, with the control of the magnetron being based on measurement of the temperature of water exiting the apparatus. When exceeding a certain limiting value, the energy supply to the magnetron is cut.

SUMMARY OF THE INVENTION

It is an object of the present invention to provide an improved apparatus for heating and thermal decontamination of pumpable or pourable material, which allows a pressure sterilization in a continuous operation.

This object and others which will become apparent hereinafter is attained in accordance with the present invention by providing in the flow passageway two force-feeding transport units, with one transport unit being situated in the flow passageway upstream of the microwave device and the other transport unit being arranged downstream of the microwave device, wherein a pressure sensor is arranged between both transport units for generating a control signal commensurate with the pressure in the conduit between the transport units and for transmitting the control signal to a control unit which is operatively connected to both transport units.

In this manner, a pressure is built up in the system via the two transport units which is maintained also in continuous operation through respective control of the drive for the transport units. Thus, pumpable or pourable materials can be conveyed in continuous operation, whereby e.g. in case pourable material are to be conveyed closed screw conveyors or the like are utilized.

For disinfection, sterilization and pasteurization of pumpable materials, the force-feeding transport units may be pumps, preferably hose pumps such as peristaltic pumps to ensure a continuous material flow through the system. The pressure in the system is controlled in dependence of the pump speed and pump power. Suitably, a holding line, e.g. in form of a pipe coil, can be arranged downstream of the microwave device, with a temperature sensor located between the microwave device and the holding line. Thus, the treatment chamber of the microwave device can be made of small dimensions since the material is passed through the holding line to maintain its temperature, with the residence time being suitably selected or controlled by means of the throughput.

The temperature sensor determines whether the material has reached the appropriate temperature before entering the holding line. A more precise control of the treatment temperature is obtained by placing a second temperature sensor at the exit of the holding line so as to sense the exit temperature of the material and determine as to whether the desired temperature has been reached during the residence time in the entire holding line.

Preferably, each temperature sensor is connected to the central control unit for control of the power of both force-feeding transport units and possibly of the magnetron of the microwave device. In this manner, the flow rate of the material can be controlled on the basis of sensed parameters in order to ensure a proper combined pressure-temperature treatment of the material.

Suitably, the material being treated may be passed upstream of the microwave device through one or more heat exchangers through which already treated material is conducted in counterflow with material to be treated. Thus, a more rapid cooling of the treated material and a pre-warming of the material to be treated is attained to thereby increase the cost-efficiency of the system.

For the same reason, in the event of utilizing a water-cooled magnetron for generating the microwave radiation, the cooling water is passed through a further heat exchanger in counterflow with the material to be treated.

In order to prevent a post-infection of already decontaminated material, an interrupter vessel is arranged within the flow passageway, preferably within the microwave device. An "interrupter vessel" is a container which is partially filled with air and interrupts the direct throughflow of material by introducing material to be treated from atop into the container, passing it through the air cushion and withdrawing it from the bottom of the container. The arrangement of the interrupter vessel within the microwave device is advantageous because accumulating material is re-heated before exiting the microwave device to ensure that sterilized material always exits the microwave device. Preferably, the interrupter vessel forms directly the treatment vessel for the pumpable material in the microwave device.

BRIEF DESCRIPTION OF THE DRAWING

The above and other objects, features and advantages of the present invention will now be described in more detail with reference to the accompanying drawing in which.

DETAILED DESCRIPTION OF A PREFERRED EMBODIMENT

Figure 1:
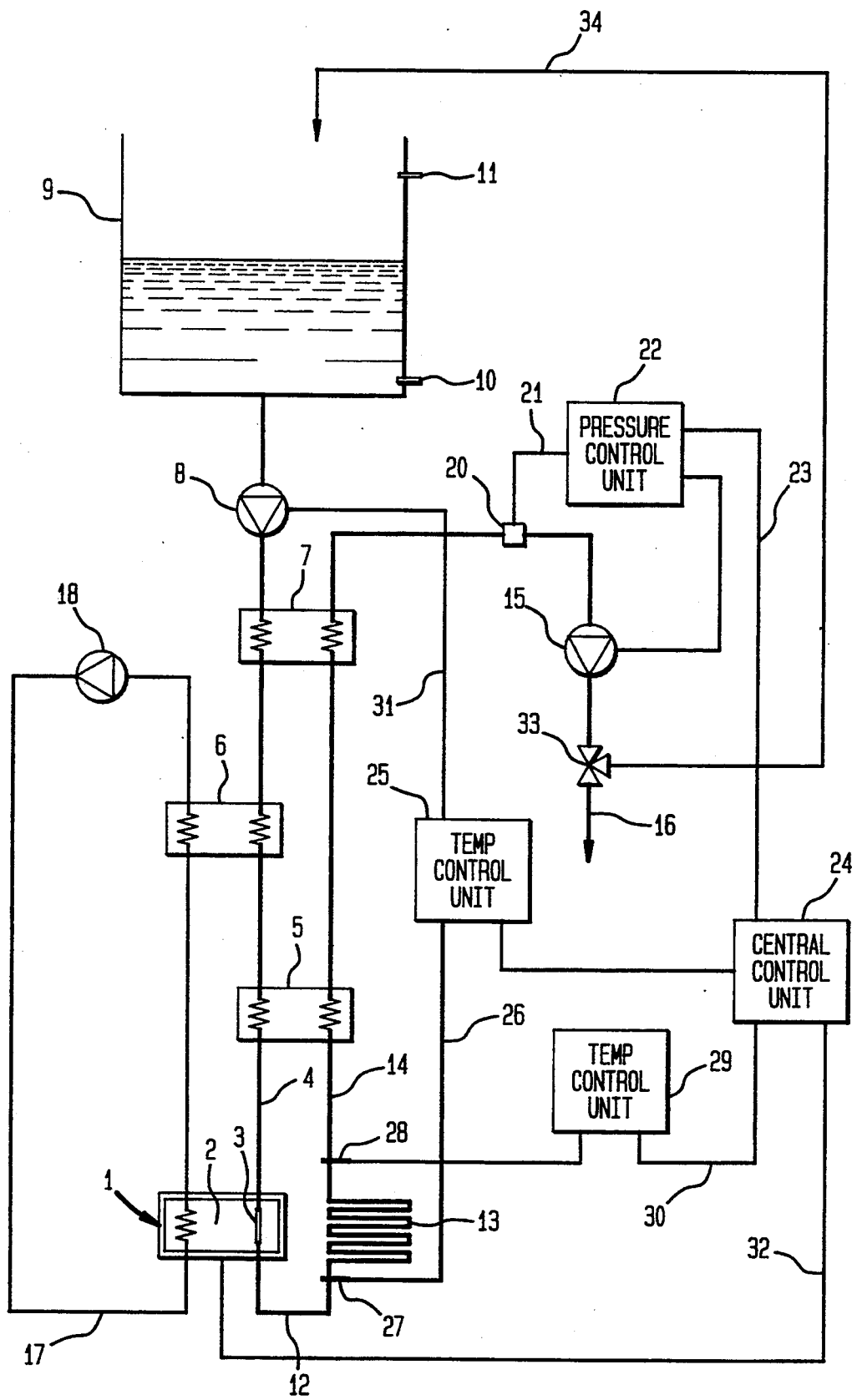
FIG. 1 is a schematic flow diagram of a decontamination apparatus in accordance with the present invention.

Referring now to the drawing and in particular to FIG. 1, there is shown a schematic flow diagram of the heating and decontamination apparatus, with reference numeral 1 generally designating a microwave device which includes a treatment chamber 3 for treatment of material (e.g. liquid medium) by microwave energy generated by a water-cooled magnetron 2. Entering the treatment chamber 3 is a conduit 4 which runs upstream of the microwave device 1 from a reservoir 9 through a cascade of heat exchangers 5, 6, 7. Material to be treated is fed from the reservoir 9 into the conduit 4 by a force-feeding pump, e.g. a hose pump or peristaltic pump 8. The reservoir 9 is provided with two level detectors 10, 11 which respectively sense the lower and upper filling level of material to effect a start or stoppage of the entire system.

After exiting the treatment chamber 3 through conduit 12, the treated material is then passed through a holding line 13, e.g. in form of a pipe coil. The residence time in the holding line 13 for maintaining the material at a desired temperature is dependent on the throughput of material through the holding line 13. Following the holding line 13 is a conduit 14 which passes through the heat exchangers 5 and 7 and leads to a second force-feeding pump 15 in form of a hose pump or peristaltic pump for pumping decontaminated material via a control valve 33 (three-way valve) through a conduit 16 to a collector. The control valve 33 is further linked to a conduit 34 by which not yet decontaminated material can be returned to the reservoir 9.

Cooling water for the magnetron 2 is circulated by a circulation pump 18 in a separate circuit which includes the heat exchanger 6. Thus, cooling water exiting the magnetron 2 through conduit 19 is passed through the heat exchanger 6 in counterflow with the material to be treated and returned to the magnetron 2 via conduit 17.

Arranged in the conduit 12 between the treatment chamber 3 and the second pump 15 is a pressure sensor 20 which is connected via a line 21 with a pressure control circuit 22. A line 23 operatively connects the pressure control circuit 22 with one input of a central control unit 24. A second input of the central control unit 24 receives data from a temperature control circuit 25 which is connected via a line 26 with a temperature sensor 27 situated at the beginning of the holding line 13. A second temperature sensor 28 is located at the exit of the holding line 13 and is connected via a further temperature control circuit 29 and a line 30 to a third input of the control unit 24. A control line 31 connects the temperature control circuit 25 with the pump 8, and a line 32 connects the control unit 24 with the current supply to the magnetron 2.

Although not shown in detail in the drawing, persons skilled in the art will understand that the microwave device 1 may also be provided with two magnetrons 2 which may be connected in series or may alternately be supplied with energy.

Figure 2:
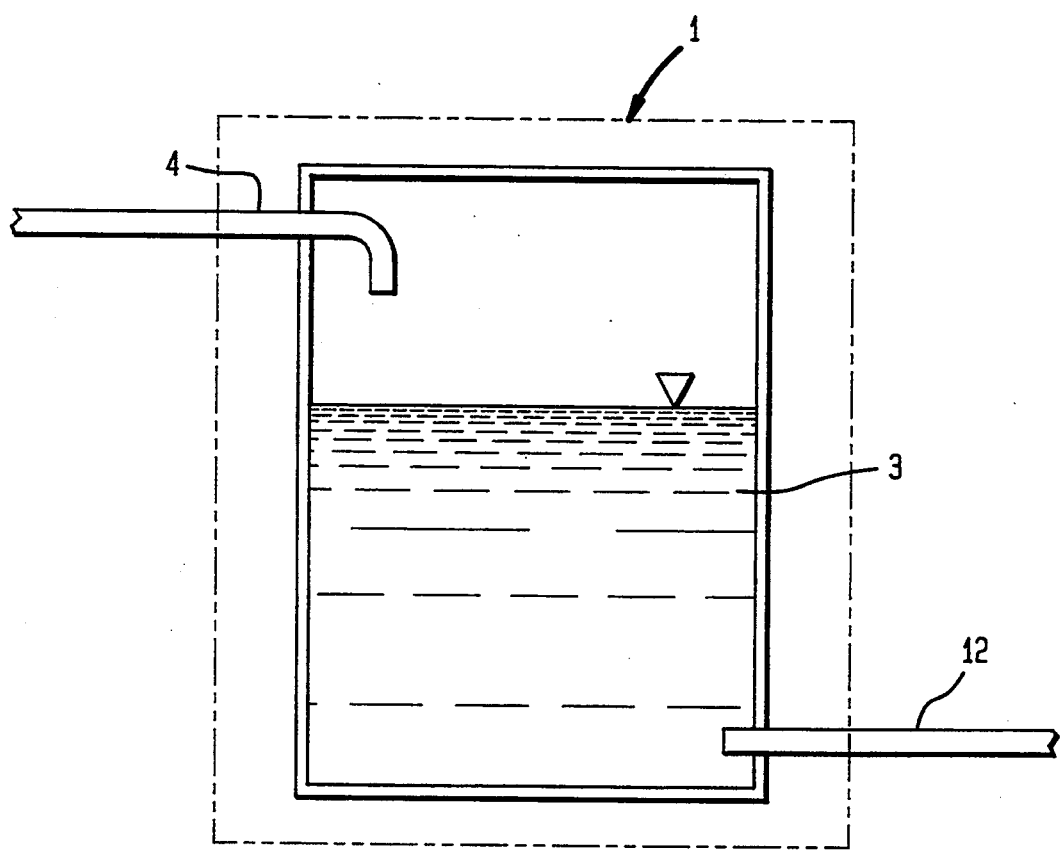
FIG. 2 is a detailed illustration of a treatment chamber of a microwave device utilized in the decontamination apparatus of FIG. 1.

Turning now to FIG. 2, there is shown an exemplified illustration of the treatment chamber 3 in form of a so-called interrupter vessel which in the present example behaves like an air chamber since the present system operates under overpressure. This interrupter vessel prevents a direct flow between the conduits 4 and 12 in order to ensure that already sterilized material in conduit 12 does not come into contact with material in conduit 4 which is not yet sterilized in case the system has to be switched off during operation. Thus, conduit 4 enters the treatment chamber 3 from atop, whereby the conduit 4 is formed in a siphon-like manner in order to prevent a discharge of material after the pump 8 is turned off. Material being treated through microwave radiation in treatment chamber 3 is collected at the bottom of the vessel and after being suitably heated exits the treatment chamber 3 through conduit 12.

It will be appreciated by persons skilled in the art that a system for pourable material is designed in a like manner, with the pump being substituted by force-feeding conveyors for solid materials, such as for example dosed conveyor screws. The use of a interrupter vessel may be omitted in such a design since a return flow of material is not a factor.

After having described the individual parts of the treatment chamber according to the present invention, its mode of operation will now be described by way of example of infectious waste water from hospitals.

The waste water to be sterilized is collected in the reservoir 9. After the waste water reaches the level of the level detector 11, the system is switched on. Pump 8 now forces material to be treated through the heat exchangers 7, 6 and 5 into the treatment chamber 3 of the microwave device 1. Pump 15 remains idle until the pressure sensor 20 registers the set working pressure, e.g. about 2 bar. Thereafter, pump 15 is operated in order to maintain a constant pressure at the pressure sensor 20. The drives of both pumps 8, 15 are controlled by the central control unit 24. Temperature sensor 27 determines whether the material contained in the treatment chamber 3 has reached a predetermined temperature value, e.g. about 120° C. at 2 bar. The desired heating is ensured by keeping the flow rate through the pump 8 during the initial phase very low and increasing it when the desired temperature value is reached. Then, the liquid is slowly passed through the holding line 13, with the temperature drop being registered by the temperature sensor 28 and inputted into the central control unit 24. As long as the temperature drop is within a certain range, i.e. waste water to be treated is kept at a selected temperature over a desired period, the system is operated until the waste water content in the reservoir 9 reaches the level of the level detector 10, at which point the system is switched off.

The material fed to the microwave device 1 via the conduit 4 is pre-warmed in the heat exchangers 7 and 5 by already treated and heated material which flows in opposite direction therethrough and in heat exchanger 6 by water which is used for cooling the magnetron 2 and flows in opposite direction through heat exchanger 6. Thus, the material to be treated is heated in a cascade-like manner, and the already treated material and water for the magnetron 2 is cooled to the desired temperature at the same time.

The provision of a heat recovery in the described manner results in an extremely cost-efficient overall system at a throughput which is about four times the throughput of conventional systems.

While the invention has been illustrated and described as embodied in an apparatus for heating and thermal decontaminating pumpable and pourable material, it is not intended to be limited to the details shown since various modifications and structural changes may be made without departing in any way from the spirit of the present invention.

What is claimed as new and desired to be protected by Letters Patent is set forth in the appended claims:

We claim:

1. Apparatus for heating and thermal decontaminating of pumpable or pourable material, comprising:
    a passageway for transporting material being decontaminated;
    a microwave unit having a treatment chamber for receiving the material transported along said passageway and subjecting the material to microwave radiation;
    first and second pump means situated in said passageway, said first pump means being arranged upstream of said treatment chamber and said second pump means being arranged downstream of said treatment chamber;
    a pressure sensor situated in said passageway between said treatment chamber and said second pump means to generate a signal commensurate with the pressure in said passageway between said first and second pump means; and
    a control unit receiving the signal from said pressure sensor and operatively connected with said first and second pump means for controlling the pressure in said passageway.

2. Apparatus as defined in claim 1 wherein said first and second pump means include force-feeding pumps.

3. Apparatus as defined in claim 2 wherein said pumps are peristaltic pumps.

4. Apparatus as defined in claim 1, and further comprising a holding line situated in said passageway downstream of said treatment chamber for maintaining the temperature of material exiting said treatment chamber, and a first temperature sensor arranged between said microwave unit and said holding line.

5. Apparatus as defined in claim 4 wherein said holding line is a pipe coil.

6. Apparatus as defined in claim 4, and further comprising a second temperature sensor situated at the end of said holding line.

7. Apparatus as defined in claim 5 wherein each of said first and second temperature sensors generate a signal commensurate with the temperature of the material and transmitted to said control unit, said signals from said pressure sensor and said temperature sensors being processed by said control unit for controlling said first and second pump means.

8. Apparatus as defined in claim 5 wherein said microwave unit includes a magnetron for producing microwave radiation in said treatment chamber, each of said first and second temperature sensors generating a signal commensurate with the temperature of the material and transmitted to said control unit, said signals from said pressure sensor and said temperature sensors being processed by said control unit for controlling said magnetron.

9. Apparatus as defined in claim 1, and further comprising heat exchanging means arranged upstream of said treatment chamber for conducting material to be treated in counterflow with already treated material.

10. Apparatus as defined in claim 9 wherein said microwave unit includes a water-cooled magnetron for producing microwave radiation in said treatment chamber, said heat exchanging means including a heat exchanger for conducting cooling water in counterflow with material to be treated.

11. Apparatus as defined in claim 1, and further comprising an interrupter vessel provided in said passageway.

12. Apparatus as defined in claim 11 wherein said interrupter vessel is placed within said microwave unit.

13. Apparatus as defined in claim 11 wherein said interrupter vessel forms said treatment chamber for pumpable material in said microwave unit.

* * * * *